United States Patent
Babel

(10) Patent No.: US 8,766,168 B2
(45) Date of Patent: Jul. 1, 2014

(54) SENSOR FOR LIQUID AND/OR GAS ANALYSIS DIRECTLY CONNECTABLE TO A HIGHER-RANKING CONTROL SYSTEM

(75) Inventor: Wolfgang Babel, Weil der Stadt (DE)

(73) Assignees: KROHNE Messtechnik GmbH, Duisburg (DE); Wolfgang Babel, Weil der Stadt (DE)

( * ) Notice: Subject to any disclaimer, the term of this patent is extended or adjusted under 35 U.S.C. 154(b) by 281 days.

(21) Appl. No.: 13/182,602

(22) Filed: Jul. 14, 2011

(65) Prior Publication Data

US 2012/0038917 A1    Feb. 16, 2012

(30) Foreign Application Priority Data

Jul. 14, 2010 (DE) ............... 20 2010 010 172 U

(51) Int. Cl.
*H01J 5/02*  (2006.01)
(52) U.S. Cl.
USPC ........................................... 250/239
(58) Field of Classification Search
USPC ........................................... 250/239
See application file for complete search history.

(56) References Cited

U.S. PATENT DOCUMENTS

| 5,727,110 | A | 3/1998 | Smith et al. |
| 5,971,282 | A | 10/1999 | Rollender et al. |
| 6,889,165 | B2 | 5/2005 | Lind et al. |
| 7,579,947 | B2 | 8/2009 | Peluso |
| 7,587,953 | B2 | 9/2009 | Wittmer |
| 7,698,609 | B2 | 4/2010 | Lalla et al. |
| 8,089,386 | B2 | 1/2012 | Konrad et al. |
| 2006/0142873 | A1* | 6/2006 | Opem et al. ............... 700/1 |
| 2006/0254911 | A1* | 11/2006 | Lindmueller et al. ...... 204/424 |
| 2008/0154101 | A1* | 6/2008 | Jain et al. ................. 600/309 |
| 2008/0211664 | A1 | 9/2008 | Griech et al. |
| 2009/0288484 | A1* | 11/2009 | Selvan et al. ............. 73/335.02 |

(Continued)

FOREIGN PATENT DOCUMENTS

| DE | 102 18 606 A1 | 11/2003 |
| DE | 102 20 450 A1 | 11/2003 |

(Continued)

OTHER PUBLICATIONS

Tong Boon Tang, et al., Toward a Miniature Wireless Integrated Multisensor Microsystem for Industrial and Biomedical Applications, IEEE Sensors Journal, vol. 2, No. 6, Dec. 2002, pp. 628-635.

(Continued)

*Primary Examiner* — Thanh Luu
(74) *Attorney, Agent, or Firm* — Roberts Mlotkowski Safran & Cole, P.C.; David S. Safran

(57) ABSTRACT

A sensor of the type for liquid and/or gas analysis, which is connected to a measuring and/or evaluating system or, respectively, to a higher-ranking control system and has a sensor housing. The circuit for the collecting, processing and transmitting measured values to the measuring and/or evaluating system or to the control system (19) are provided in the sensor housing (2). This circuit has analog sensor electronics (3), an analog-digital converter (14) for converting the detected analog measured values into digital measured values, a processing unit (15) and communication device (17) for processing and transmitting the digital measured values to the measuring and/or evaluating system or to the control system (19) according to a standard communication protocol of process technology.

3 Claims, 1 Drawing Sheet

(56) References Cited

U.S. PATENT DOCUMENTS

| | | |
|---|---|---|
| 2010/0234706 A1 * | 9/2010 | Gilland .................... 600/344 |
| 2011/0060463 A1 * | 3/2011 | Selker et al. ............... 700/266 |
| 2011/0204876 A1 | 8/2011 | Mieth et al. |
| 2011/0208440 A1 | 8/2011 | Pechstein et al. |

FOREIGN PATENT DOCUMENTS

| | | |
|---|---|---|
| DE | 10 2004 009 734 A1 | 9/2005 |
| DE | 10 2006 020 341 A1 | 10/2007 |
| DE | 10 2006 062 184 A1 | 6/2008 |
| WO | 2005/031339 A1 | 4/2005 |
| WO | WO 2009158702 A2 * | 12/2009 |

OTHER PUBLICATIONS

P.D. Wilson et al., Applications of a Universal Sensor Interface Chip (USIC) for Intelligent Sensor Applications, 1995 The Institution of Electrical Engineers, Printed and Published by the IEE, Savoy Place, London WC2R 0BL, UK, 6 Pages.

* cited by examiner

SENSOR FOR LIQUID AND/OR GAS ANALYSIS DIRECTLY CONNECTABLE TO A HIGHER-RANKING CONTROL SYSTEM

BACKGROUND OF THE INVENTION

1. Field of the Invention

The invention relates to a sensor for liquid and/or gas analysis, which is connected to a measuring and/or evaluating system or, respectively, to a higher ranking control system and which has a sensor housing.

2. Description of Related Art

Sensors of the type described above are known in different forms from the prior art. A liquid sensor having a sensor housing is thus known from PCT Patent Application Publication WO 2005/031339 and corresponding U.S. Pat. No. 7,587,953 that is connected in a contact-free manner via a coupling to a transducer and further to a measuring and/or evaluating system. A receiving sensor for collecting measured values, a pre-processing unit for pre-processing the collected values, an analog-digital converter for converting the collected analog measured values into digital measured values and means (modem, power supply unit, inductor or radio module) for contact-free transmission of the digital measured values to the transducer are located in the sensor housing. The coupling has means (inductor or radio module, amplifier, modem) for receiving the contact-free transmitted digital measured values and an interface for transmitting the measured values to the transducer. The contact-free transmission of the measured values between the sensor and the coupling serves, in particular, the galvanic de-coupling of the sensor from the measuring and/or evaluating system.

Liquid and/or gas sensors have a relatively short operating life and thus have to be regularly exchanged. For economic reasons, it has been attempted in previous years to relocate as much of the electronics as possible from the sensor into the coupling. For this reason, the transmitter part of the transducer is arranged in the coupling or is implemented there, for example, by means of a processor or a computer program running on the processor in the known liquid and/or gas sensors. For economic reasons, the electronics are thus split into sensor electronics, on the one hand, and cable-connection electronics, on the other hand, in which essentially the sensor signals are converted into a proprietary protocol in order to be able to then transmit them to the measuring and/or evaluating system. The interface between the liquid and/or gas sensor and the cable (for example, via a coupling for contact-free signal transmission) is costly and causes technical problems in respect to ambient conditions.

SUMMARY OF THE INVENTION

Based on the above described prior art, the object of the invention is to provide a sensor of the type in the introduction, which primarily makes it possible to implement the entire system consisting of the sensor and the measuring and/or evaluating system or, respectively, the higher-ranking control system in a more economical manner.

The sensor according to the invention, in which the object derived and shown above is met, is first and foremost characterized in that circuit means for the collecting, processing and transmitting measured values to the measuring and/or evaluating system or, respectively, to the control system are provided in the sensor housing, that the circuit means comprises analog sensor electronics, an analog-digital converter for converting the detected analog measured values into digital measured values, a processing unit and communication means for processing and transmitting the digital measured values to the measuring and/or evaluating system or respectively, to the control system according to a standard communication protocol of process technology.

While in the type of prior art, to which the sensor and the measuring and/or evaluating system, or respectively, the higher-ranking control system, the entire system as well as the above-described coupling and the transducer belong, the sensor according to the invention is designed in such a manner that the coupling and a transducer subordinate to the coupling are no longer necessary. This is made possible in that the sensor housing not only houses the analog sensor electronics, but an analog-digital converter, a processing unit and communication means are also provided for processing and transmitting the digital measured values to the measuring and/or evaluating system, or respectively, to the control system according to a standard communication protocol of process technology.

The sensor according to the invention is intended for liquid and/or gas analysis. This means that it can be designed for measuring the pH-value, the conductivity, the oxygen content, the chlorine content, the ozone content, the hydrogen peroxide content, the content of free chlorine, the content of residual chlorine, the turbidity and/or the solids content in the liquid or respectively, gas or as a photometer or as a spectrometer.

In the sensor according to the invention, the described circuit means are preferably implemented at least partially as ASIC (application specific integrated circuit).

The sensor according to the invention is preferably connected via a plug or in some other manner with detachable wiring to the measuring and/or evaluating system, or respectively, to the control system. A PLC (programmable logic controller), a control system that controls or regulates the process to be controlled or regulated cyclically, or an asset management system for anti-cyclical tasks in the process to be controlled or regulated, e.g., for diagnostic tasks (advanced diagnostics), the setting of parameters, determining the point in time of necessary cleaning or calibration can also belong to the control system. The sensor can either be directly or indirectly, for example via a segment coupler, connected to the control system.

In the sensor according to the invention, the circuit means provided in the sensor housing can be galvanically connected to one another. However, it is also possible to provide a galvanic separation, namely between the analog-digital converter and the processing unit and/or between the processing unit and the communication means. The galvanic separation can, for example, be implemented in that a transformer is provided as part of the electrical circuit in the sensor housing, via which an inductive transmission can occur on its primary inductor, on the one hand and on its secondary inductor, on the other hand. The galvanic separation can, however, also be opto-electronic.

As described, the communication means for processing and transmitting the digital measured values to the measuring and/or evaluating system, or respectively, the control system belong to the sensor according to the invention, namely according to a standard communication protocol of process technology. This, of course, can be carried out in different manners. On the one hand, the communication means can transmit the digital measured values according to one of the following described field bus communication protocols to the control system: HART, Profibus PA, Profibus DB, Foundation Field Bus in 2-wire technology. On the other hand, however, there is the possibility of implementing the communication between the communication means and the measuring and/or evaluating system or, respectively, the control system via a wireless interface, in particular according to the wireless HART, WLAN, ZigBee or RFID standard.

A field bus joins field devices in one system such as sensing elements (sensors) and actuating elements (actuator) for means of communication with a measuring and/or evaluating system or, respectively, with a control system. When multiple communication members send their messages with the same wire, then it has to be specified who (identification), what (measured value, command) and when (initiative) "has the say". There are standard protocols for this. Field bus technology was developed in the 1980s in order to replace the parallel wiring of binary signals that was common up to that point as well as the analog transmission of signals with digital transmission technology. Today, there are many different field bus systems with different features established on the market. Field buses in the standard IEC 61158 ("Digital data communication for measurement and control—field bus for use in industrial control system") have been standardized worldwide since 1999. Multiple sensors and actuators are often required for controlling a system. Should the control occur electrically, the questions arises how the sensors and actuators are to be joined to the control device. Two basic variations are possible:

a) Parallel wiring—for each sensor and actuator, a cable is run from the control device (control system, normally DCS (distributed control system)).

b) Serial wiring—only one cable is run from the control device (DCS via PLC); the cable is led past each sensor and actuator.

Due to the greater number of input and output points, the wiring complexity increases for parallel wiring with the increasing degree of automation in a system or machine. This is linked with complex project planning, installation, startup procedure and maintenance. The requirements on the cables are often so high, e.g., that special cables are installed for the transmission of analog values. In this manner, parallel wiring has become a serious cost and time factor in automation technology. In comparison, serial wiring of the components in the field section by means of so-called field bus systems is significantly more economical. The field bus replaces the parallel wires or, respectively, wire packages or cables or cable packages with one single bus cable and joins all levels, from the field level to the control level. Regardless of the type of automation device, for example, programmable logic controllers from different producers or PC-based controls, the transmission medium of the field bus links all components together. These can be arbitrarily distributed in the field, since they are all connected decentralized on-site.

The sensor according to the invention has been described essentially in respect to its function or functions up to this point. However, the constructive design can also be of importance. Insofar, a further teaching of the invention to that effect is that in the sensor according to the invention, the sensor housing is designed in the shape of a hollow cylinder and has a diameter of 12 mm. Additionally, in the sensor according to the invention, the sensor housing can consist preferably of plastic, stainless steel, glass or ceramic.

In view of construction, a preferred design of the sensor according to the invention is characterized in that the circuit means provided in the sensor housing are provided at least partially on a flexible printed circuit board. Here, the printed circuit board can have multiple layers, preferably is designed as a sandwich panel.

The sensor according to the invention is preferably designed for operational conditions of about +65° C. to +130° C. operation temperature and about 6 to 8 bar operation pressure.

Additionally, the sensor according to the invention is, more exactly, the electronics provided in the sensor housing preferably have a modular construction. It is also possible, for example, to break down the electronics into an analog module (sensor electronics), a digital module (calculating unit, computer) and a communication module (processing and transmitting the digital measured values to the measuring and/or evaluating system or the control system). Preferably, the modules can be combined with one another in respect to different sensor systems and communication, so that the electronics for arbitrary types of sensors as well as for arbitrary communications according to standard communication protocols of process technology can be compiled with existing modules. The modules can also be designed as FPGAs (field programmable gate array) as direct input for an ASIC design. The digital module and/or the communication module can also be implemented as a one-chip solution, which allows for further miniaturizing the circuit inside of the sensor housing. Different circuit parts can belong to the ASIC, for example flash memory, ROM, RAM, EEPROM, CPU, A-D converter, HART modem and/or components belonging to a Profibus or a Foundation Field Bus.

As already stated, in view of construction, a preferred design of the sensor according to the invention is characterized in that the sensor housing is designed in the shape of a hollow cylinder and has a diameter of 12 mm. This allows the sensor to be used in a standard installation normally used in process technology and to be replaced easily and quickly. All of the process facilities (fittings, holders, etc.) are normally designed for a sensor diameter of 12 mm. In some industries, e.g., wastewater and water industry, sensors are normal that have diameters of up to 45 mm, typically 25 mm and 45 mm, and in some exceptions even up to 100 mm. The sensors are typically 120 mm, 225 mm or even 420 mm long.

If, as is already described further above, the circuit means provided in the sensor housing are at least partially provided on a flexible printed circuit board, the limited space available inside of the sensor housing can be particularly efficiently used. It is possible, for example that the flexible printed circuit board extends along the round cross-sectional form of a long sensor housing having a hollow cylindrical shape.

If the particularly preferred design is implemented, in which the printed circuit board has multiple layers, preferably designed as a sandwich panel, different boards of the sandwich panel can be galvanically decoupled. A galvanic separation between the analog-digital converter and the communication means can be present in a one-board solution. The printed circuit board can be designed as a multi-layer board, a 1- or 2-side board, a rigid/flexible board or a HDI-SBU multi-layer board (HDI=high density interconnection, SBU=sequential build-up).

In a particularly advantageous design, the sensor according to the invention is designed for use in areas at risk of explosion and/or at risk of fire damping. Here, the sensor meets the necessary requirements for an ATEX certification (ATEX=Atmosphere Explosible). These are defined, for example, in the standard EN 50014 as well as in the standard guidelines RiLi 94/9EG and RiLi 1999/92/EG. The compliance of the ATEX certification can be controlled by various certification authorities (PTB=Physikalisch-Technische Bundesanstalt, TÜV=Technischer Überwachungsverein, FM=Factory Mutual, CSA=Canadian Standard Association).

Finally, the sensor according to the invention can also be designed for meeting the requirements of SIL2. The sensor according to the invention then meets high requirements in operation safety (fail safe) and has a SIL2 certificate (SIL2=safety integrity level 2). Requirements for a SIL2 certificate are defined in the standards EN 61508 and EN 61511.

In detail, there are a number of possibilities for designing and further developing the sensor according to the invention. Here, please refer to the patent claims subordinate to patent claim 1 and to the following description of a preferred embodiment in conjunction with the drawing. The drawing shows:

DETAILED DESCRIPTION OF THE INVENTION

Figure 1:
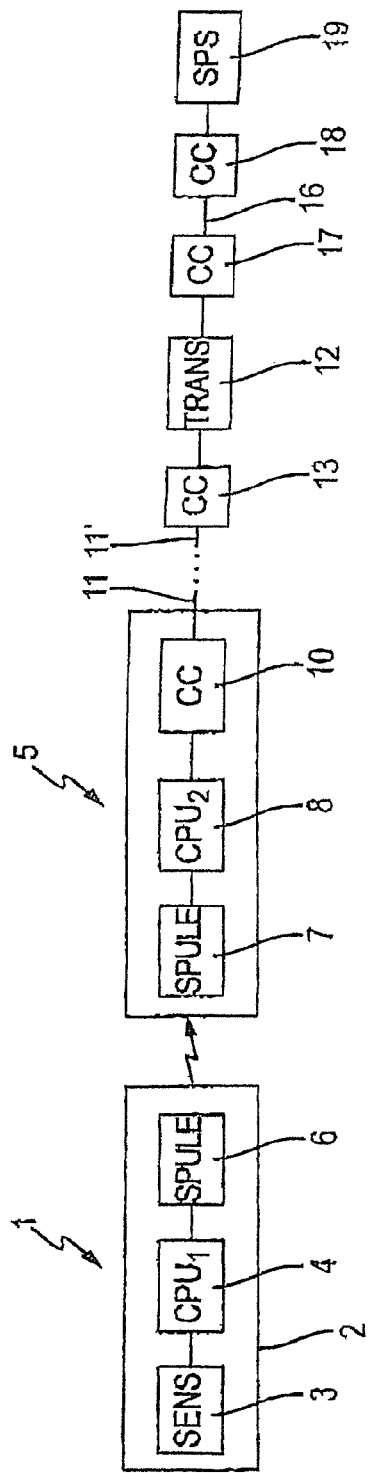
FIG. 1 schematically depicts a sensor known from the prior art.

FIG. 1 shows a known sensor 1 that has a sensor housing 2 that is made of plastic or stainless steel. Sensor electronics 3 are provided inside of the sensor housing 2, which are designed and arranged to collect analog measured values using the sensor 1. The sensor 1 is designed for liquid analysis, for example, for measuring the pH value, the conductivity, the oxygen content, the chlorine content, the ozone content, the hydrogen peroxide content, the content of free chlorine, the content of residual chlorine, the turbidity and/or the solids or gas content in the liquid or is used as a photometer or as a spectrometer.

Of course, the sensor 1 can be used for gas analysis using a respective design of the sensor electronics.

In the known sensor 1 shown in FIG. 1, a first processing unit is provided in the form of a processor 4, which, inter alia, converts the analog measured values into corresponding digital measured values. The processor 4 does not have to be particularly productive, since its essential task is to process the collected measured values for contact-free transmission to a coupling element 5. In the shown embodiment, the wireless transmission to the coupling element 5 occurs inductively. For this purpose, the sensor 1 also has a first inductance 6. A further inductance 7 is provided in the coupling element 5. A second processing unit in the form of a processor 8, which processes the digital measured values for transmission via a proprietary communication protocol, is subsequent to the inductance 7. The processed measured values are transmitted to a communication controller 10 of a bus system 11. The measured values are then transmitted via the bus system 11 according to a proprietary communication protocol to a further communication controller 13 assigned to a measuring and/or evaluating system 12.

A transmitter, a measured value transducer and/or converter belong to the measuring and/or evaluating system 12; it normally carries out all important calculations, e.g., signal main processing, sample recognition, sensor diagnostic, noise suppression or reduction, sensor calibration, filtering, feature extraction. The processed data are first transmitted to a higher-level control system 19 after the main evaluation in the measuring and/or evaluating system 12. The measuring and/or evaluating system 12 is a relatively large box arranged outside of the sensor 1. Data transmission between the measuring and/or evaluating system 12 and the control system 19 occurs via a bus system 16 having communication controllers 17, 18 using typical transmission protocols from process technology (e.g., HART, Profibus PA, Foundation Field Bus, etc.).

The control system 19 includes, for example, a programmable logic controller (PLC) or a so-called asset management system. The control system 19 no longer carries out processing or manipulation of the measured values, in particular, the control system 19 does not change the measured values at all. Moreover, the control system 19 only collects the measured values and uses them, if necessary together with other measured values from other sensors or with saved information about the process, for process control or process regulation, for example the control of actuators, e.g., of valves, electromagnets or similar components.

The known sensor has a relatively short lifespan, and thus, needs to be replaced from time to time. The sensor 1 can be mechanically affixed in the coupling element 5 and electrically and signally connected in order to simplify replacement as well as to galvanically separate the sensor electronics 3 from the measuring and/or evaluating system. Signal transmission occurs contact-free via both inductances 6, 7. In the sensors 1 known from the prior art, it is attempted to shift as much of the electronics as possible from in the sensor housing 2 to the outside, e.g., into the coupling element 5 or the external measuring and/or evaluating system 12, in order to make the sensors 1 more economical.

Figure 2:
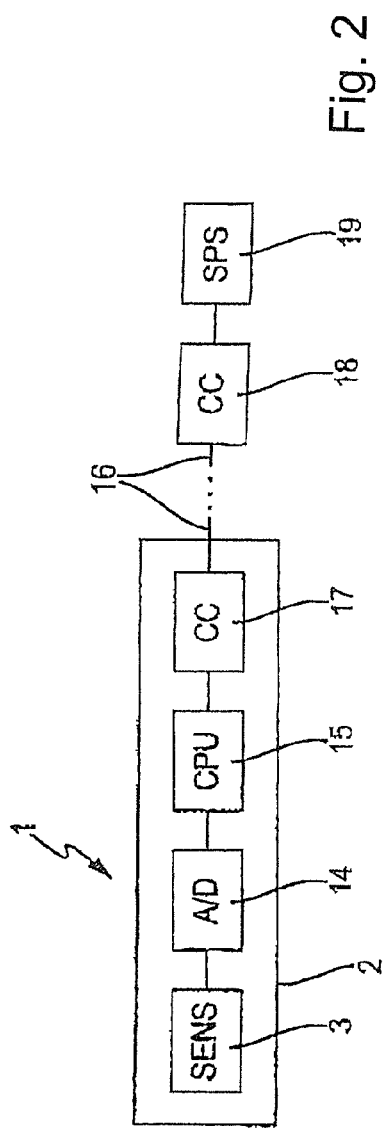
FIG. 2 schematically depicts a preferred embodiment of a sensor according to the invention.

In the sensor 1 according to the invention shown in FIG. 2, a very different solution is chosen. Here, the goal is to integrate as much of the electronics as possible into the sensor 1. The sensor 1 according to the invention 1 in FIG. 2 includes a sensor housing 2, in which the sensor electronics 3 are provided for collecting analog measured values. The sensor electronics 3 are designed essentially the same as in the known sensors, e.g., as in sensor 1 in FIG. 1. The analog measured values collected by the sensor electronics 3 are also converted into digital measured values by an analog-digital converter 14 also provided in the sensor housing 2. These are then given to a calculating unit, for example, in the form of a processing unit 15, which carries out a pre-processing of the measured values and further processing for the transmission to the external control system 19 according to a standard communication protocol of process technology via a bus system 16. It is also possible that the analog-digital converter 14 is bodily and/or functionally integrated in the processing unit 15.

The processing unit 15 is joined to a communication means 17 of the bus system 16, which puts the processed measured values on the transmission path of the bus system 16. The measured values are then transmitted via the bus system 16 to a communication controller 18 assigned to the control systems 19 according to a standard communication protocol of process technology.

According to the invention, the entire functionality of the external measuring and/or evaluating system 12 of the known sensor 1 and the coupling 5 from FIG. 1 is relocated in the sensor 1 in FIG. 2 and implemented there by the sensor electronics 3, the analog-digital converter 14, the processing unit 15 and/or the communication means 17. In particular, the functionality of transmitter, measured value transducer and/or converter is integrated into the processing unit 15 and/or the communication means 17. All processing, calibration, sensor diagnostic, etc. takes place in the sensor 1 itself The processed and prepared measured values are then directly transmitted to the control system 19 and are used, shown or otherwise issued there for controlling or regulating a process. In the sensor according to the invention, no further manipulation of the sensor-measured values occurs outside of the sensor 1.

Due to the special design of the sensor 1 according to the invention, the use of the measuring and/or evaluating system 12 is no longer required. Instead, only a simpler and more economical analog-digital converter 14 is used. Additionally, according to the invention, one transmission path of the known sensor 1 can be omitted, i.e., the path which runs from the processing unit 8 to the measuring and/or evaluating unit 12 and via which that data transmission occurs according to a proprietary protocol. Instead, in the sensor 1 according to the invention, the digital measured values are transmitted directly to the control system 19 via the bus system 16 by means of a typical communication protocol of process technology.

In order to keep the costs of replacing sensors 1 from time to time as low as possible, it is preferably provided to design the electronics integrated in the sensor 1 as an ASIC. In this manner, it is possible to implement the sensor electronics 3, the analog-digital converter 14, the processing unit 15 (including periphery components) and the communication means 17 in one ASIC (so-called mixed mode with analog and digital components in one ASIC). It is also possible to discretely implement the sensor electronics 3 conventionally and to only implement the digital components, i.e., the analog-digital converter 14, the processing unit 15 and the communication means 17, on an ASIC. It is even possible to implement the communication means 17 discretely, in particular when this implements a data transmission according to the HART protocol. In the implementation of a data transmission according to the protocol Profibus CA or the protocol Profibus DB it is more likely, for economical and spatial reasons at this point in time, to use ASIC for the implementation.

Additionally, the analog-digital converter 14 and the processing unit 15 can be implemented in a first ASIC and the communication means 17 in another ASIC. This implementation with a separate communication means 17 could be practical, in particular for data transmission via the bus system 16 according to the standard HART, the standard Profibus PA, the standard Profibus DB or the standard Foundation Field Bus. Finally, it is also possible to implement only the processing unit 15 (including periphery components) on a first ASIC and the other components (sensor electronics 3, analog-digital converter 14 and communication means 17) on another ASIC or on multiple further ASICs or on an FPGA or on multiple further FPGAs or discretely. Should the individual components and circuit parts of the sensor be available more compact and economical in the future that they can all be arranged without great expense in a sensor housing 2, it is also possible to implement the sensor electronics 3, the analog-digital converter 14, the processing unit 15 and the communication means 17 of the sensor completely discretely, i.e., without an ASIC.

The electronics of the sensor 1 according to the invention can be designed in modules, wherein individual modules of the electronics can be designed as FPGAs. The size of ASICs and/or FPGAs can be chosen depending on space available in the sensor housing 2. The dimensions can, for example, be about 1.2 cm×2 cm, 1.5 cm×2.5 cm, 1 cm×5 cm or 1 cm×10 cm, to name a few. The boards used for ASICs and/or FPGAs can be designed having multiple parts, wherein the individual board parts can be moveably affixed to one another. To moveably affix the individual board parts, conductor paths formed on the printed circuit board or corresponding foil conductors can be used, for example. Preferably, the partial boards are galvanically decoupled from one another. However, it is possible that flexible printed circuit boards, e.g., foil conductors are used and the boards for ASICs and/or FPGAs. In this manner, the space inside of the sensor housing 2 can be used particularly advantageously.

In the sensor 1 according to the invention, the sensor housing 2 is preferably formed as a hollow cylinder of plastic or stainless steel and preferably has a diameter of 12 mm, so that the sensor 1 can be installed in standard facilities as are common in process technology. All of the electronics are designed in such a manner that they fit into one sensor housing 2 with a diameter of 12 mm. This is advantageous in that the same electronics can be installed in any sensor housing 2, i.e. in sensors having a diameter from 12 mm to 45 mm, in individual cases even up to 100 mm.

The sensor according to the invention is preferably designed for use in areas at risk of explosion (ARTEX certification according to EN 50014, RiLi 94/9/EG and RiLi 1999/92/EG). Additionally, the sensor according to the invention has high operation safety (fail safe) (SIL2 certification according to EN 61508 and EN 61511). The SIL2 suitability of the sensor 1 according to the invention requires a special circuit outlay. However, it is also possible to do without the SIL2 suitability of the sensor 1.

As already described further above, the sensors according to the invention can be installed at operating temperatures from 65° C. to 130° C. and operating pressure from 6 bar to 8 bar.

What is claimed is:

1. Sensor for at least one of liquid and gas analysis, which is connected directly to a higher-ranking control system, comprising:
   a sensor housing, and
   circuit means for collecting, processing and transmitting measured values to the higher-ranking control system provided in the sensor housing,
   the circuit means comprising means for measuring a pH-value, analog sensor electronics, an analog-digital converter for converting detected analog measured values into digital measured values, a processing unit and communication means for processing and transmitting the digital measured values to said higher-ranking control system according to a communication protocol, and
   wherein means for galvanic separation are provided both between said analog-digital converter and the processing unit and between the processing unit and said communication means.

2. Sensor according to claim 1, wherein the communication means is adapted for transmitting the digital measured values to said higher-ranking control system according to the HART field bus communication protocol in two-wire technology.

3. Sensor according to claim 1, wherein the sensor housing is in the shape of a hollow cylinder having a diameter of 12 mm.

* * * * *